(12) United States Patent
Spicer et al.

(10) Patent No.: US 6,225,298 B1
(45) Date of Patent: May 1, 2001

(54) COMPOSITIONS AND METHODS FOR CONTRACEPTION AND FOR TREATMENT OF BENIGN GYNECOLOGICAL DISORDERS

(75) Inventors: Darcy V. Spicer, Pasadena; Malcolm Cecil Pike, Long Beach; John R. Daniels, Pacific Palisades, all of CA (US)

(73) Assignee: Balance Pharmaceuticals, Inc., Pacific Palisades, CA (US)

( * ) Notice: Subject to any disclaimer, the term of this patent is extended or adjusted under 35 U.S.C. 154(b) by 0 days.

(21) Appl. No.: 08/878,690

(22) Filed: Jun. 18, 1997

Related U.S. Application Data

(63) Continuation of application No. 08/343,383, filed on Nov. 22, 1994, now abandoned.

(51) Int. Cl.⁷ .................................................. A61K 31/56
(52) U.S. Cl. ........................... 514/170; 514/179; 514/843
(58) Field of Search ..................... 514/170, 179, 514/843

(56) References Cited

U.S. PATENT DOCUMENTS

| | | |
|---|---|---|
| 3,453,296 | 7/1969 | Wettstein et al. . |
| 3,541,137 | 11/1970 | Los . |
| 3,549,671 | 12/1970 | Laurent et al. . |
| 3,721,685 | 3/1973 | Jolly et al. . |
| 3,789,087 | 1/1974 | Weichert . |
| 3,818,093 | 6/1974 | Hahn . |
| 4,259,325 | 3/1981 | Prezewowsky et al. . |
| 4,670,426 | 6/1987 | Zor et al. . |
| 4,753,794 | 6/1988 | Donahoe . |

OTHER PUBLICATIONS

Medline Abstract AN: 85229276, Levine et al. 1985.*
Medline Abstract AN: 94073341, Weiss 1993.*
Dox "Melloni's Illustrated Medical Dictionary," p. 60, 1979.*
Klijn, J. G. M. et al., *Cancer Research* 49:2851–2856 (1989).
Michna, II. et al., *J. Steroid Biochem. Molec. Biol.* 43:203–210 (1992).
Nieman, L. K. et al., *N. Engl. J. Med.* 316:187–191 (1987).
Kettel, L. M. et al., *Fertil. Steril.* 56:402–407 (1991).
Kekkonen, R. et al, *Fertil. Steril.* 53:747–750 (1990).
Kekkonen, R. et al., *Fertil. Steril.* 60:610–615 (1993).
Pike, M.C. et al., *Epidemiol. Rev.* 15:17–35 (1993).
Longacre, T.A. & Barlow, S.A., *Am. J. Surg. Path.* 10:382–393 (1986).
Anderson, T.J. et al., *Br. J. Cancer* 46:376–382 (1982).
Preston–Martin, S. et al., *Cancer Res.* 50:7415–7421 (1990).
Pollow, K. et al., *Contraception* 40:213–32 (1989).
Haider, S. & Inbaraj, R.M., *Gen Comp Endocrinol* 73, 92–5 (1989).
Ferenczy, A. et al., *Am J. Obstet Gynecol* 133, 859–67 (1979).

\* cited by examiner

*Primary Examiner*—Russell Travers
*Assistant Examiner*—S. Wang
(74) *Attorney, Agent, or Firm*—Christie, Parker & Hale, LLP

(57) ABSTRACT

Compositions and methods for use in preventing conception or treating benign gynecological disorders, wherein an effective amount of an antiprogestational agent [e.g., progesterone (progestin, progestogen, gestagen) antagonist or progesterone synthesis inhibitor] administered over a first period of time is combined with an effective amount of a progestogen for a second period of time. The antiprogestational agent is selected from single agents or mixtures thereof. The progestogen is selected from single agents or mixtures of natural or synthetic progestogens. The formulations are effective as contraceptive agents and for treatment of benign gynecological disorders including uterine fibroids, premenstrual syndrome, dysfunctional uterine bleeding, polycystic ovarian syndrome and endometriosis.

23 Claims, No Drawings

COMPOSITIONS AND METHODS FOR CONTRACEPTION AND FOR TREATMENT OF BENIGN GYNECOLOGICAL DISORDERS

CROSS-REFERENCE TO RELATED APPLICATION

This is a file wrapper continuation of Application No. 08/343,383, filed Nov. 22, 1994, now abandoned.

BACKGROUND OF THE INVENTION

This invention relates to compositions and methods useful for contraception and for treatment of benign gynecological disorders in mammals, especially human females. More particularly, the present invention is directed to contraceptive methods and methods of treating benign gynecological disorders and preparations for use therein which are effective for reducing exposure to progestational agents.

The first progestogen antagonist synthesized and tested was RU 486[RU 38486; 17-hydroxy-11-(4-dimethylaminophenyl)-17-(prop-1-ynyl)estra -4,9-dien-3-one; beta-[(4-N,N-dimethylamino)-phenyl]-17β-hydroxy-17α-propynyl-4,9(10)-oestradiene-3-one; mefepristone]. Mifepristone has high affinity for the progesterone receptor, with predominantly antiprogestational effects. Mifepristone is known to have growth-inhibitory effects in breast cancer cells in in vitro and in vivo preclinical studies and in human clinical trials [Klijn, J. G. M. et al., *Cancer Research* 49:2851–2856 (1989)]. Other antiprogestational agents have been synthesized and tested including ZK 98.299 (onapristone) and ZK 112.993, which also have antitumor efficacy [Michna, H. et al., *J. Steroid Biochem. Molec. Biol.* 43:203–210 (1992)].

Mifepristone is known to be useful as a medical abortifacient (because of its antiprogestational activities) and as a postcoital contraceptive. Mifepristone has been evaluated as a potential contraceptive agent using several schedules. A single dose of mefepristone late in the menstrual cycle may be a useful contraceptive approach [Nieman, L. K. et al., *N. Engl. J. Med.* 316:187–191 (1987)].

Protracted (i.e., 3 month) administration of 100 mg per day mefepristone alone to premenopausal women has been shown to inhibit ovulation and ovarian progesterone production, while maintaining early follicular phase levels of estradiol, estrone and testosterone [Kettel, L. M. et al., *Fertil. Steril.* 56:402–407 (1991)]. These effects may be mediated through a progesterone agonist effect of mefepristone on the hypothalamic-pituitary unit, although other mechanisms are possible.

Several new regimens of progesterone antagonists and progestins have been described. One such regimen [Kekkonen, R. et al, *Fertil. Steril.* 53:747–750 (1990)] consists of 25 mg of mefepristone on days 1 to 14 of a 28-day treatment cycle followed by norethisterone on days 15 to 24 of the cycle. A subsequent report describes a regimen consisting of 25 mg of mefepristone on days 1 to 21 of a 31-day treatment cycle followed by norethisterone 5 mg per day or medroxyprogesterone acetate 5 mg per day taken on days 22 to 31 [Kekkonen, R. et al., *Fertil. Steril.* 60:610–615 (1993)].

These administration sequences are designed to mimic the physiological secretion of steroids in the menstrual cycle, with a progestational steroid administered over a 10 day period following 14 to 21 days of administration of the progestogen antagonist. With such a regimen, approximately 30% of days are associated with exposure to the progestogen.

PCT Patent Applications WO 93/21926 and 93/21927 to Hodgen (the entire disclosures of which are hereby incorporated by reference) describes the protracted administration of a progestogen, with administration of an antiprogestational compound on the 28th or 30th day of the treatment cycle. The contraceptive compositions described by Hodgen provides for an even greater number of days of exposure to the progestogen component than in the normal menstrual cycle.

The breast has a tightly regulated pattern of growth primarily under the control of steroid hormones. The effects of steroid hormones on the normal breast are increasingly well understood. Estrogen induces some breast epithelial proliferation, but estrogen and progesterone together produce even greater cell proliferation [Pike, M.C. et al., *Epidemiol. Rev.* 15:17–35 (1993)]. In non-pregnant premenopausal women the breast epithelium undergoes repetitive periods of cell proliferation and cell loss secondary to cyclic ovarian activity. In the terminal duct lobular unit (TDLU) of the premenopausal breast, cell proliferation is low during the follicular phase of the menstrual cycle. Following ovulation, progesterone is produced by the corpus luteum and TDLU cell proliferation increases two- to three-fold over follicular levels [Pike et al. (1993), *supra*]. Consistent with the breast cell proliferation rates, the size and number of terminal ductules peak during the late-luteal phase [Longacre, T. A. & Barlow, S. A., *Am. J. Surg. Path.* 10:382–393 (1986)]. If fertilization and pregnancy do not ensue, progesterone levels fall, the rate of breast cell division decreases, and a wave of cell death by apoptosis follows the peak in cell proliferation [Anderson, T. J. et al., *Br. J. Cancer* 46:376–382 (1982)].

Proliferating cell populations are more susceptible to carcinogenic effects, and the rise in cancer risk associated with cell proliferation is secondary to an increased chance of mutation and loss of tumor suppressor genes [Preston-Martin, S. et al., *Cancer Res.* 50:7415–7421 (1990)]. Thus, breast cancer risk would be predicted to increase the greatest during periods of exposure to both estrogen and progestogen, as in the premenopausal period or in women receiving combined oral contraceptives (COCs); less during periods of exposure only to estrogen, as in postmenopausal women receiving estrogen replacement therapy (ERT) or in obese postmenopausal women; and least during periods of exposure to very low levels of both hormones, as in non-obese postmenopausal Asian women.

The heretofore-identified regimens comprising administration of an antiprogestational agent in sequence with a progestogen are thus not entirely satisfactory. In particular, they result in exposure to progestogens for a period of time similar to a normal menstrual cycle, and to a similar or greater amount of progestational action. As such, they may result in a breast cancer risk similar to or possibly greater than that of a normal ovulating woman.

U.S. Pat. No. 5,211,952 to Spicer et al. (the entire disclosure of which is also hereby incorporated by reference) describes administration of a progestational agent every two months to six months, with administration of a gonadotropin hormone releasing hormone and an estrogen.

It is an object of the present invention to provide regimens for contraception and the treatment of benign gynecological disorders which would obviate the problems attendant to the use of existing methods of birth control and treatment regimens.

In particular, it is an object of the present invention to reduce the risk of adverse consequences associated with the heretofore known methods.

BRIEF DESCRIPTION OF THE INVENTION

In accordance with the present invention, there are provided methods for contraception and for treating benign gynecological disorders which comprise administering over an extended period of time (on the order of about 6 weeks to about 26 weeks) an amount of an antiprogestational agent (e.g., a progestational antagonist or progesterone synthesis inhibitor) effective at suppressing ovulation or ovarian progesterone production and/or at blocking the effects of progesterone, followed by a short-term administration (on the order of about 5 to 21 days, preferably 10 to 15 days) of an amount of a progestational steroid effective to counteract the possibility of endometrial hyperstimulation, hyperplasia or carcinoma which may develop during prolonged therapy with estrogenic steroids. The reduction in the amount of progestogen administered has the effect of reducing the projected rate of breast cancer incidence, as well as treating or reducing the incidence of various benign gynecological disorders.

DETAILED DESCRIPTION OF THE INVENTION

The present invention eliminates problems inherent in the heretofore-proposed gonadotropin releasing hormone plus estrogen and periodic progestin treatment. The antiprogestational agents may be administered by mouth. Furthermore, as the antiprogestational agents do not suppress ovarian estrogen and androgen production, there is no need for replacement of these steroid hormones.

Pursuant to one preferred embodiment of the present invention, the contraceptive or treatment regimen comprises either a daily administration or a formulation designed for continuous use over an extended period of time. Typically, the formulations of the invention are effective for use over at least about 6 weeks. Depending on the composition, the inventive formulation may be effective for as long as about 6 months. It is presently preferred that the formulation be effective over about a 2 to 3 month period.

For purposes of the present invention, an "antiprogestational agent" is defined as a composition which impedes or eliminates the effects of progesterone in a patient being treated therewith. This may be effected in one of two general ways. A progesterone antagonist interacts with progesterone receptors to prevent a progestogen's biological effects on known target tissues such as breast, myometrium and endometrium. Progesterone antagonists may additionally suppress ovulation and ovarian progesterone production. Progesterone synthesis inhibitors block the ovarian production of progesterone without necessarily blocking the effect of the progestogen at the tissue level.

A number of compounds have been developed to act as progesterone antagonists, including but not limited to the following: mifepristone (RU 486; 17-hydroxy-11-(4-dimethylaminophenyl)-17- (prop-1-ynyl)estra-4,9-dien-3-one; β-[(4-N,N-dimethyl amino)-phenyl]-17β-hydroxy-17α-propynyl-4,9(10)- oestradiene-3-one); onapristone (ZK 98.299); ZK 112.993[11-4 (4-acetylphenyl)-17-hydroxy-17-(-propynyl)-,9-diene-3-one]; Org 31710 [(6α,11β,17β)-11-(4-NMe$_2$-phenyl)-6-Me-4',5'-dihydrospiro[oestra-4,9-diene-17,2(3'H)-furan]-3-one];Org 33628[(11β,17α)-(4-acetylphenyl)- 17,23-epoxy-19,24-dinorchola-4,9,20-trien-3-one]; Org 31806 [(7β,11β,17β)-11-(4-NMe$_2$-phenyl)-7-Me-4',5'-dihydrospiro(oestra -4,9-diene-17,2'(3'H)-furan)-3-one]; and lilopristone (ZK 98734). These and other potentially useful agents are described in, e.g., the following publications: the aforementioned PCT applications WO 93/21926 and WO 93/21927; U.S. Pat. No. 4,386,085; U.S. Pat. No. 4,027,019; U.S. Pat. No. 4,000,273; U.S. Pat. No. 3,890,356; U.S. Pat. No. 3,622,622; U.S. Pat. No. 3,983,144; U.S. Pat. No. 3,462,466; U.S. Pat. No. 3,790,564; U.S. Pat. No. 4,231,946; Pollow, K. et al., *Contraception* 40:213–32 (1989); and Michna et al. (1992), supra, the entire disclosures of which are hereby incorporated by reference. The progesterone antagonist mefepristone is commercially available in a number of countries and is in clinical trials in the United States.

Also contemplated as within the scope of the present invention are inhibitors or antagonists of progesterone synthesis, which block the production of progesterone. Examples of suitable progesterone synthesis inhibitors include, but are not limited to, the following: trilostane, epostane, azastene and cyanoketone [PCT applications WO 93/21926 and WO 93/21927; Haider, S. & Inbaraj, R. M., *Gen Comp Endocrinol* 73, 92–5 (1989)].

To identify additional antiprogestational agents suitable for use in the compositions and methods of the present invention, it is further possible to employ heretofore-known biological assays for such agents. An exemplary assay is described in Michna, H. et al., *J.Steroid Biochem. Molec. Biol.* 38:359–365 (1991) for progesterone antagonists. In this bioassay rats are subjected to ovariectomy on day 1. On day 8 the experimental rats are administered estrone, progesterone and the progesterone antagonist daily. On day 11 the animals are sacrificed and the number of tubular alveolar buds in the inguinal mammary gland counted in a whole mount preparation using a 40-fold magnification. Potent progesterone antagonists inhibit the proliferative action of the progesterone and reduce the number of tubular alveolar buds by 30 to 35% or more.

A suitable dose of the antiprogestational agent may be readily identified. For antagonists that block ovulation and for progesterone synthesis inhibitors, the lowest dose of the composition that eliminates the known rise in serum progesterone during the second half of the normal menstrual cycle is appropriate. With reference to the exemplary antagonist mefepristone (RU486), this dose would be in the range of about 10 to about 100 mg per day. Similarly, with reference to the exemplary progesterone synthesis inhibitor epostane, this dose would be in the range of about 600 to about 1000 mg per day. For antagonists that do not block ovulation, a dose of the composition that eliminates the antimitotic effects of progesterone and decidualization of the endometrium during the second half of the normal menstrual cycle would be appropriate [Ferenczy, A. et al., *Am J. Obstet Gynecol* 133, 859–67 (1979)].

As would be readily understood by those working in the field, the amount of the antiprogestational agent effective to achieve the desired results may readily be determined empirically with respect to any given antiprogestational agent and for any given mammal. The effective dose ranges, as well as being compound specific, may also depend upon patient characteristics, such as age and weight. Further, the effective amount of the antiprogestational agent also depends upon route of administration. In general, it is expedient to administer the active antiprogestational agent in an amount between about 0.001 and 10 mg/kg of body weight per day.

The second component of the invention is a progestogen (progestational agent). Unlike the antiprogestational agent, which is administered at a continuous level for an extended period of time, the progestogen is administered in an amount sufficient to provide suitable systemic levels for only a second, more limited period of time. Typically, the progestogen is administered for a period of time on the order of 5 to 21 days, and preferably 10 to 15 days. The progestogen is provided in an amount effective to inhibit ovulation (and the rise in serum progesterone) and to minimize or eliminate the occurrence of endometrial hyperplasia by substantially reducing the possibility of endometrial hyperstimulation which may occur during prolonged treatment with antiprogestational agents without a period of exposure to the beneficial endometrial effects of a progestogen.

Unlike the heretofore-proposed regimens, administration of progestogen in preferred embodiments of the present invention is generally not repeated every 28–31 days (corresponding to the length of the normal menstrual cycle). Rather, the progestogen component is provided in these preferred embodiments only for a short period of time comprising a portion of each extended treatment regimen cycle. Suitably, an extended treatment cycle in accordance with the present invention comprises about six weeks to about 26 weeks, and most preferably two or three months, with the progestogen administration comprising only about 5 to about 21 days, and preferably about 10 to about 15 days, of the extended treatment cycle.

Suitable progestational agents (progestogens) for use in accordance with the present invention are described in greater detail in the aforementioned U.S. Pat. No. 5,211,952. These include, but are not limited to, the following: dydrogesterone, ethynodiol diacetate, hydroxyprogesterone caproate, medroxyprogesterone acetate, norethindrone, norethindrone acetate, norethynodrel, norgestrel, progesterone, megesterol acetate, gestodene, desogestrel, cingestol, lynestrenol, quingestanol acetate and chlormadinone. Typical dose ranges for progestogens depend upon the choice of steroid and the individual patient. For example, for an adult human female administered norethindrone, typically 1 mg is given by mouth daily during the period of progestogen administration. Alternatively, systemic administration of the progestogen component may be completely avoided, for example by the use of an intrauterine device which releases the progestogen within the uterus. It is presently preferred that the progestogen be administered at a rate effective to provide serum levels equivalent to serum levels of progesterone of from about 5 to about 20 ng/ml, and preferably about 5 to about 15 ng/ml, during the time interval of progestogen treatment.

Administration of formulations in accordance with the present invention in depot form may be effected in a manner well known per se, for example as described in the aforementioned U.S. Pat. No. 5,211,952. Similarly, formulations for daily administration may be prepared in a conventional manner by incorporating the active materials into suitable carrier substances. Carrier substances may be organic or inorganic materials which are suitable for enteral or parenteral application and which do not enter into reactions with the active agents. Suitable carrier agents include, but are not limited to, water, alcohols, vegetable oils, polyethylene glycols, lactose, starch, talcum, gelatin, magnesium stearate, sodium lauryl sulfate, etc.

The invention may be better understood with reference to the accompanying examples, which are intended for purposes of illustration only and should not be construed as in any sense limiting the scope of the invention as defined in the claims appended hereto.

Example 1

In a contraceptive product for oral administration over a twelve week period, the antiprogestational agent mefepristone is administered as a tablet in a daily dose sufficient to inhibit ovulation (50 mg) for 71 days, followed by the progestogen norethisterone as a tablet in a daily dose sufficient to induce a non-proliferative endometrium (1 mg) for 14 days. Both agents are suitably provided in a convenient pill dispenser package.

Example 2

In a contraceptive pellet for subcutaneous administration, mefepristone is administered as a cholesterol pellet to achieve a daily dose of 25 mg for 90 days. The mefepristone/cholesterol pellet is coated with norethisterone in palmitic acid to achieve a daily dose of 0.75 mg per day for 14 days. The superficial norethisterone coat is absorbed over approximately the first 14 days followed by the mefepristone over approximately 90 days.

What is claimed is:

1. A method for preventing conception comprising:
   administering an antiprogestational agent, at a level effective to inhibit ovulation, over a first period of time of about six weeks to about twenty-six weeks; and
   administering a progestational agent, at a level effective to inhibit endometrial proliferation, over a second period of time of about five to about twenty-one days immediately following, immediately preceding, or running concurrently with a portion of said first period of time.

2. A method according to claim 1, wherein said progestational agent is selected from the group consisting of dydrogesterone, ethynodiol diacetate, hydroxyprogesterone caproate, medroxyprogesterone acetate, norethindrone, norethindrone acetate, norethynodrel, norgestrel, progesterone, megesterol acetate, gestodene, desogestrel, cingestol, lynestrenol, quingestanol acetate and chlormadinone.

3. A method according to claim 1, wherein said first period of time is about two months to about three months.

4. A method according to claim 1, wherein said second period of time is about ten days to about fifteen days.

5. A method according to claim 1, wherein the second period of time is less than thirty percent of the first period of time.

6. A method according to claim 1, wherein the second period of time immediately follows or immediately precedes the first period of time.

7. The method of claim 1 wherein said first period of time is about two to about three months, and said second period of time is about ten days to about fifteen days.

8. A method according to claim 1, wherein the antiprogestational agent is selected from the group consisting of mifepristone, onapristone, 11-4(4-acetylphenyl)-17-hydroxy-17-(propynyl)-9-diene-3-one, (6α,11β,17β)-11-(4-NMe$_2$-phenyl)-6-Me-4',5'-dihydrospiro[oestra-4,9-diene-17,2'(3'H)-furan]-3-one, (11β,17α)-11-(4- acetylphenyl)-17,23-epoxy-19,24-dinorchola-4,9,20-trien-3-one, (7β,11β,17β)-11-(4-(NMe$_2$-phenyl)-7- Me-4',5'-dihydrospiro(oestra-4,9-diene-17,2'(3'H)-furan)-3-one, lilopristone, trilostane, epostane, azastene and cyanoketone.

9. A method according to claim 8, wherein said antiprogestational agent is selected from the group consisting of mifepristone, onapristone, and 11-4(4-acetylphenyl)-17-hydroxy-17-(-propynyl)-, 9-diene-3-one.

10. A method for treating a non-malignant gynecological disorder where suppression of ovulation and/or suppression of ovarian progesterone production is therapeutic, the method comprising:
    administering an antiprogestational agent, at a level effective to inhibit ovulation, over a first period of time of about six weeks to about twenty-six weeks; and administering a progestational agent, at a level effective to inhibit endometrial proliferation, over a second period of time of about five to about twenty-one days immediately following, immediately preceding, or running concurrently with a portion of said first period of time.

11. A method according to claim 10, wherein the progestational agent is selected from the group consisting of dydrogesterone, ethynodiol diacetate, hydroxyprogesterone caproate, medroxyprogesterone acetate, norethindrone, norethindrone acetate, norethynodrel, norgestrel, progesterone, megesterol acetate, gestodene, desogestrel, cingestol, lynestrenol, quingestanol acetate and chlormadinone.

12. A method according to claim 10, wherein the antiprogestational agent is selected from the group consisting of mifepristone, onapristone, 11-4(4-acetylphenyl)-17-hydroxy-17-(propynyl)-9- diene-3-one, (6α,11β,17β)-11-(4-NMe$_2$-phenyl)-6-Me-4',5'-dihydrospiro -3-one, (11β, 17α)-11-(4-acetylphenyl)-17,23-epoxy-19,24-dinorchola-4, 9,20-trien-3-one, (7β,11β,17β)-11-(4-(NMe$_2$-phenyl)-7-Me-4',5'-dihydrospiro(oestra-4,9-diene-17,2'(3'H)-furan)-3-one, lilopristone, trilostane, epostane, azastene and cyanoketone.

13. A method according to claim 10, wherein the first period of time is about two months to about three months.

14. A method according to claim 10, wherein the second period of time is about ten days to about fifteen days.

15. A method for treating a non-malignant gynecological disorder, comprising:

administering an antiprogestational agent, at a level effective to inhibit ovulation, over a first period of time of about six weeks to about twenty-six weeks; and administering a progestational agent, at a level effective to inhibit endometrial proliferation, over a second period of time of about five to about twenty-one days immediately following, immediately preceding, or running concurrently with a portion of said first period of time;

wherein the benign gynecological disorder is selected from the group consisting of uterine fibroids, premenstrual syndrome, dysfunctional uterine bleeding, polycystic ovarian syndrome and endometriosis.

16. The method of claim 15 wherein said first period of time is about two to about three months, and said second period of time is about ten days to about fifteen days.

17. A method for treating a non-malignant gynecological disorder, comprising:

administering an antiprogestational agent, at a level effective to inhibit ovulation, over a first period of time of about six weeks to about twenty-six weeks; and administering a progestational agent, at a level effective to inhibit endometrial proliferation, over a second period of time of about five to about twenty-one days immediately following, immediately preceding, or running concurrently with aportion of said first period of time;

wherein the benign gynecological disorder is selected from the group consisting of uterine fibroids, premenstrual syndrome, dysfunctional uterine bleeding, and polycystic ovarian syndrome.

18. The method of claim 17 wherein said first period of time is about two to about three months, and said second period of time is about ten days to about fifteen days.

19. A method for suppressing ovulation and/or ovarian progesterone production comprising:

administering an antiprogestational agent, at a level effective to inhibit ovulation, over a first period of time of about six weeks to about twenty-six weeks; and administering a progestational agent, at a level effective to inhibit endometrial proliferation, over a second period of time of about five to about twenty-one days immediately following, immediately preceding, or running concurrently with a portion of said first period of time.

20. A method according to claim 19, wherein the progestational agent is selected from the group consisting of dydrogesterone, ethynodiol diacetate, hydroxyprogesterone caproate, medroxyprogesterone acetate, norethindrone, norethindrone acetate, norethynodrel, norgestrel, progesterone, megesterol acetate, gestodene, desogestrel, cingestol, lynestrenol, quingestanol acetate and chlormadinone.

21. A method according to claim 19, wherein the antiprogestational agent is selected from the group consisting of mifepristone, onapristone, 11-4(4-acetylphenyl)-17-hydroxy-17-(propynyl)-9- diene-3-one, (6α,11β,17β)-11-(4-NMe$_2$-phenyl)-6-Me-4',5'-dihydrospiro[oestra-4,9-diene-17,2'(3'H)- furan]-3-one, (11β, 17α)-11-(4-acetylphenyl)-17,23-epoxy-19,24-dinorchola-4,9,20-trien-3-one, (7β,11β,17β)-11-(4-(NMe$_2$-phenyl)-7-Me-4',5'-dihydrospiro(oestra-4,9-diene-17,2'(3'H)-furan)-3-one, lilopristone, trilostane, epostane, azastene and cyanoketone.

22. A method according to claim 19, wherein the first period of time is about two months to about three months.

23. A method according to claim 19, wherein the second period of time is about ten days to about fifteen days.

* * * * *

UNITED STATES PATENT AND TRADEMARK OFFICE
CERTIFICATE OF CORRECTION

PATENT NO.    : 6,225,298 B1                                    Page 1 of 1
DATED         : May 1, 2001
INVENTOR(S)   : Darcy V. Spicer, Malcolm Cecil Pike and John R. Daniels It is certified that error appears in the above-identified patent and that said Letters Patent is hereby corrected as shown below:

Title page,
Item [56], References Cited, U.S. PATENT DOCUMENTS, insert the following references:

| | | | | |
|---|---|---|---|---|
| -- | 3,462,446 | 8/1969 | De Wald | 260/295 |
| | 3,622,622 | 11/1971 | De Wald | 260/501.18 |
| | 3,790,564 | 2/1974 | Pierdet | 260/239.55 |
| | 3,890,356 | 6/1975 | Grunwell et al. | 260/397.5 |
| | 3,983,144 | 9/1976 | Leemhuis | 260/397.3 |
| | 4,000,273 | 12/1976 | Grunwell et al. | 424/238 |
| | 4,027,019 | 5/1977 | Shroff | 424/238 |
| | 4,231,946 | 11/1980 | Ponsold et al. | 260/397.4 |
| | 4,386,085 | 5/1983 | Teutsch et al. | 424/238 --. |

-- FOREIGN PATENT DOCUMENTS
    WO 93/21926   11/1993   PCT
    WO 93/21927   11/1993   PCT --.

Column 8,
Line 5, replace "aportion" with -- a portion --.

Signed and Sealed this

Twenty-sixth Day of August, 2003

JAMES E. ROGAN
*Director of the United States Patent and Trademark Office*